United States Patent [19]

Herrmann et al.

[11] Patent Number: 5,421,323
[45] Date of Patent: Jun. 6, 1995

[54] ENDOSCOPE WITH ADDITIONAL VIEWING APERTURE

[75] Inventors: Uwe Herrmann, Berlin; Manfred Boebel, Oetisheim, both of Germany

[73] Assignee: Richard Wolf GmbH, Knittlingen, Germany

[21] Appl. No.: 157,781

[22] Filed: Nov. 24, 1993

[30] Foreign Application Priority Data

Dec. 2, 1992 [DE] Germany .................... 42 41 643.4

[51] Int. Cl.⁶ .................................................. A61B 1/04
[52] U.S. Cl. ........................................ 128/4; 128/5; 128/7
[58] Field of Search ....................................... 128/4–8, 128/10, 11; 606/13, 15, 46

[56] References Cited

U.S. PATENT DOCUMENTS

| 879,224 | 2/1908 | Wappler | 128/7 |
| 2,018,335 | 10/1937 | Wappler | 606/46 |
| 2,112,056 | 3/1938 | Wappler | 128/7 |
| 2,487,498 | 11/1949 | Wallace | 128/7 |
| 3,850,175 | 11/1974 | Iglesias | 128/7 |
| 3,942,530 | 3/1976 | Northeved | 128/4 |
| 4,137,920 | 2/1979 | Bonnet | 128/7 |
| 4,867,138 | 9/1989 | Kubota et al. | 128/6 |
| 4,905,670 | 3/1990 | Adair . | |

FOREIGN PATENT DOCUMENTS

| 1166019 | 11/1958 | France | 128/6 |
| 702374 | 2/1941 | Germany | 128/6 |
| 3616193 | 11/1986 | Germany | 128/6 |
| 1214084 | 2/1986 | U.S.S.R. | 128/6 |

OTHER PUBLICATIONS

Richard Wolf GmbH, "Pan Hysteroskop", E/-Gynäkologie, 12/VI. 83 d, 1983.
H. Bülow et al., "Urologisches Endoskop zur Laser Therapie", *Technik in the Medizin/Arzttechnik*, Verlag für Medizin Dr. Ewald Fischer GmbH, Heidelberg.
Yoshihiro Hayata et al., "Anwendung von Hämatoporphyrinderivaten und Laserbestrahlung bei der Diagnose und Therapie von Neoplasmen", *Acta Medicotechnika*, 29th Annual Publication, No. 4, 1981, pp. 127–129.
Richard Wolf GmbH, Urologie '88, D 618/lx. 88, 1988, p. 7.

*Primary Examiner*—Richard J. Apley
*Assistant Examiner*—John Leubecker
*Attorney, Agent, or Firm*—Panitch, Schwarze, Jacobs & Nadel

[57] ABSTRACT

An endoscope has a tubular shaft for receiving a viewing lens and a treatment instrument. The shaft has a distal end portion of channel-shape, providing a viewing window for the viewing lens. The circumference of the shaft is of oval cross-section around which the wall of the channel-shaped portion extends asymmetrically. An aperture recess forming an additional viewing window for the viewing lens is provided in the wall of the end portion. The endoscope is particularly suitable for use in endoscopic operations in the female breast, since the additional viewing window allows inspection of an implant before opening a capsule surrounding the implant.

10 Claims, 3 Drawing Sheets

ENDOSCOPE WITH ADDITIONAL VIEWING APERTURE

BACKGROUND OF THE INVENTION

This invention relates to an endoscope comprising a tubular shaft for the introduction thereinto of a viewing lens and a treatment instrument, the shaft having a distal end portion which is channel-shaped and provides a viewing window for the viewing lens.

The present invention proceeds from a pan hysteroscope such as is marketed, for example by Richard Wolf GmbH of Knittlingen, Germany, and in which, a viewing lens and a treatment instrument are arranged adjacent to each other within the shaft. As the distal end portion of the shaft is channel-shaped, both the lens and instrument are protected on one side, while on the other side, that is to say, the open side of the channel-like portion, the lens and the instrument are exposed in such a way that in use the instrument can be deflected in the direction of the open side or displaced axially. Flexible forceps, a laser transmission optical fibre or the like may constitute the treatment instrument, for the endoscopic examination and treatment of the uterus, for example.

Silicone implants are commonly used, in particular for breast reconstruction. Such silicone implants, may, however, occasionally become encapsulated, within the breast. There may also be damage to the implant. In such cases, it is usual to check the implant surgically, release the encapsulation or, if occasion should arise, exchange the implant.

It is an object of the present invention to provide an endoscope which allows of both visual checking of the implant and release of the encapsulation, as well as, should occasion arise, the performance of other operations particularly in the region of the female breast, endoscopically and with sufficient safety and hence with minimum invasion.

SUMMARY OF THE INVENTION

According to the invention this is achieved by providing in the channel-shaped distal end portion of the shaft, a recess forming an additional viewing window for the viewing lens.

This allows of endoscopic operations in the region of the female breast, involving the inspection of an implant and release of a capsule surrounding the implant. Other operations may, however, also be carried out with such an endoscope, for example, the removal of tissues, or for other diagnostic operations. The surgeon introduces the shaft of the endoscope in the region of the nipple and can then first inspect the implant without open surgery and, if occasion arises, open an encapsulation surrounding the implant as well. In all such endoscopic operations, the implant must be protected. To this end the channel-shaped end portion of the shaft shields both the viewing lens and the treatment instrument, for example a laser transmission fibre, on one side, since contact between the fibre and the implant must be avoided. In order to avoid such contact reliably, however, the duck's bill shape, that is to say the channel-shape of the distal end portion of the shaft alone, is insufficient, because when opening the capsule, the implant must be kept permanently in sight. To this end the additional viewing window is provided in said channel-shaped portion of the shaft, in order to give the implant the necessary protection, and at the same time to enable visual checking of the implant, or at least of part of it.

The surgeon can therefore observe the implant permanently during opening of the capsule. The channel-like shape of the end portion of the shaft also ensures that the treatment instrument can always be moved and inserted only in its axial direction or in the direction away from the implant, that is to say, towards the open side of the channel profile of said end portion of the shaft, and that the instrument itself slides along the implant.

Although a laser transmission fibre is preferably used as the treatment instrument, an HF probe or a mechanical instrument, for example forceps or a combined instrument, may also be used. The use of a laser transmission optical fibre supplied, for example, by means of a neodymium-YAG laser has proved itself in particular for the opening of a capsule.

Preferably, the shaft is of essentially oval cross-section, the channel-shaped end portion being so configured that it encloses the major semi-axis of said oval cross-section. The oval cross-sectional shape of the shaft, in comparison with a round cross-sectional shape of the same diameter, affords the advantage of a smaller circumference and hence less stress on the surgical opening. The viewing lens and treatment instrument can be arranged adjacent to each other in the shaft in such a way that the viewing lens directly adjoins said channel-shaped shaft portion so that a clear view through the additional viewing window and a clear view of the treatment instrument and the tissue location being treated thereby is ensured.

The distal end of the shaft is, as far as possible, of a rounded shape in order to allow it to slide inside the breast with as little friction and injury thereto as possible. Preferably, however, the channel-shaped end portion of the shaft is additionally provided with a sloped distal end face, in order to allow of easier advance of the shaft in the axial direction within the breast, this being further assisted by the supply of flushing liquid.

Particularly during the opening of an implant capsule, the channel-shaped end portion of the shaft preferably extends not as is usual in hysteroscopes only through a circumferential angle of about 180°, but through such an angle of at least 200°, whereby the distal ends of viewing lens and treatment instrument are better protected so that damage to the implant is excluded to a very great extent. In this case it is preferable that the channel profile of the distal end portion of the shaft is asymmetrical, part of the wall of said profile being extended on one side of the major axis of said oval cross-section. Preferably, also the recess forming the additional viewing window is located in said extended part of the wall. Thus, during the opening of a capsule not only the implant itself, but also the position of the implant relative to the capsule can be checked by virtue of the additional viewing window.

If the recess has an approximately oval contour as seen in plan view, it can provide a large enough opening and the risk of injury can be kept low. The risk of injury can further be reduced by providing the distal end of the shaft with an inclined end face at the junction between the shaft and said channel-shaped distal end portion.

In order to fix the viewing lens reliably within the shaft and to avoid contact between the lens and the treatment instrument, the lens may be introduced into, and fixed in, a tube of approximately D-shaped cross-section within the shaft. Especially if the treatment instrument is a laser transmission optical fibre, an additional tube can be provided in the shaft, for guiding the optical fibre, the additional tube abutting against the flat side of the D-cross-section tube within the shaft. If the D-cross-section tube is arranged eccentrically in the shaft, space will remain therein for the introduction of an additional treatment instrument. In order to avoid collision between the additional instrument and the sensitive laser transmission optical fibre, in the distal region of the shaft, a guide for the additional instrument may be provided in the distal end of the shaft, the guide being in the form of a wedge for deflecting the additional instrument away from the optical fiber as the additional instrument emerges from the distal end of the shaft. The shaft may be provided with pipes or conduits for flushing liquid.

A preferred embodiment of the present invention will now be described by way of example with reference to the accompanying drawings.

DETAILED DESCRIPTION OF THE PREFERRED EMBODIMENT OF THE INVENTION

Figure 1:
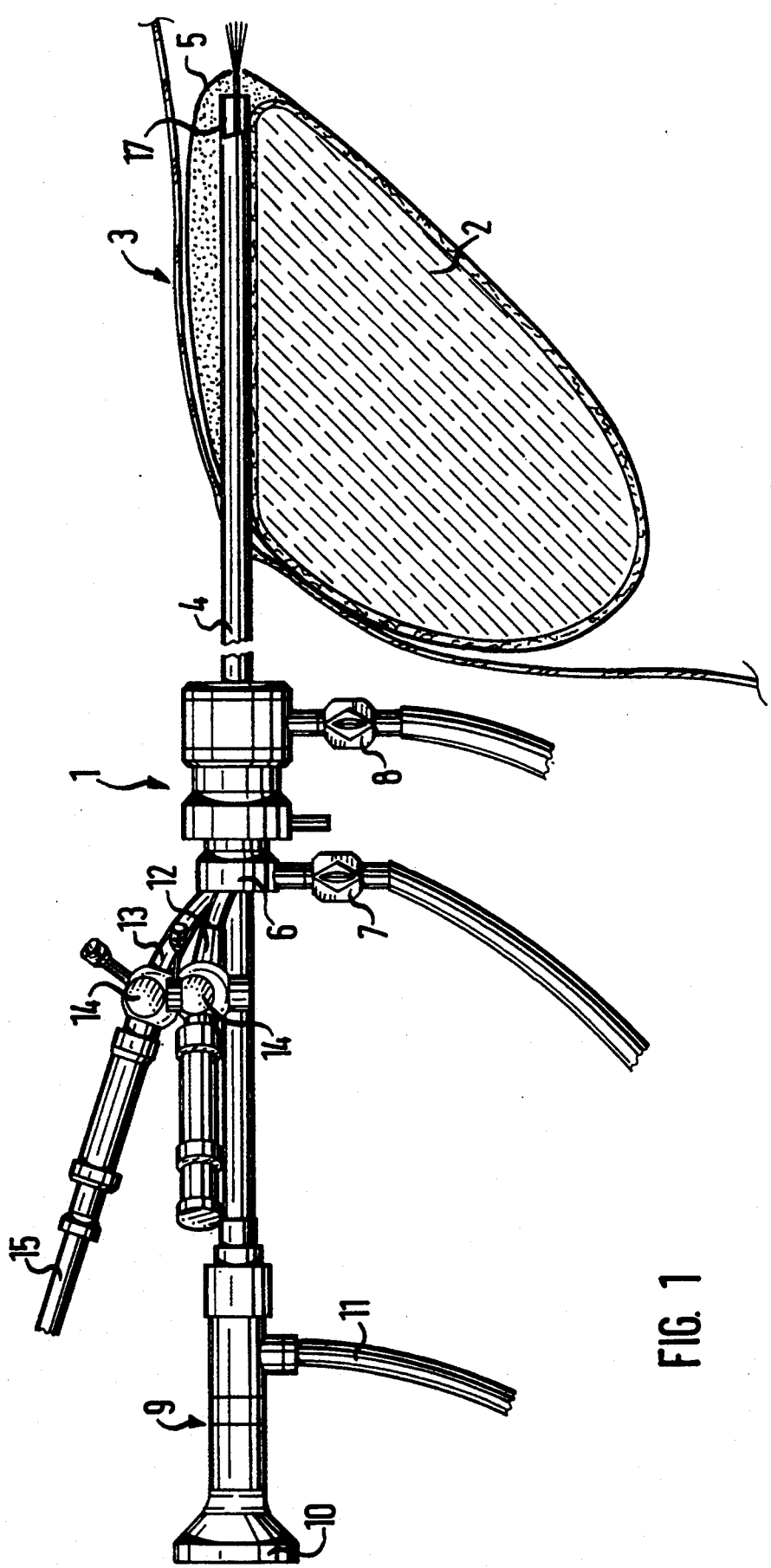
FIG. 1 is a schematic side view of an endoscope according to the preferred embodiment of the invention, in use in a surgical operation.

FIG. 1, shows an endoscope 1 according to the preferred embodiment, in use in opening a capsule 5 surrounding an implant 2 within a female human breast 3. A shaft 4 of the endoscope has been introduced into the breast 3 through an incision in the region of the nipple thereof. The endoscope 1 is basically constructed as a hysteroscope.

A flushing connection 7 and a suction connection 8 are provided at the proximal end 6 of the shaft 4, through which flushing liquid can be conducted to the distal end of the shaft 4 and conducted away again. A central tube 9 is provided for the introduction and fixing of a viewing lens (not shown) in the distal end region of the shaft 4. The tube 9 has thereon an eyepiece 10 and a lighting connection 11, for the viewing lens. Instrument introduction conduits 12 and 13 extending at an angle from the proximal end 6 of the shaft 4 are each provided with a closure tap 14. The conduit 13 receives a first treatment instrument in the form of an optical fibre 15 for conducting laser light for performing the cutting operation, the distal end of the fibre 15 being located at the distal end of the shaft 4.

Figure 3:
FIG. 3 is a view taken on the lines III—III of FIG. 2.
Figure 6:
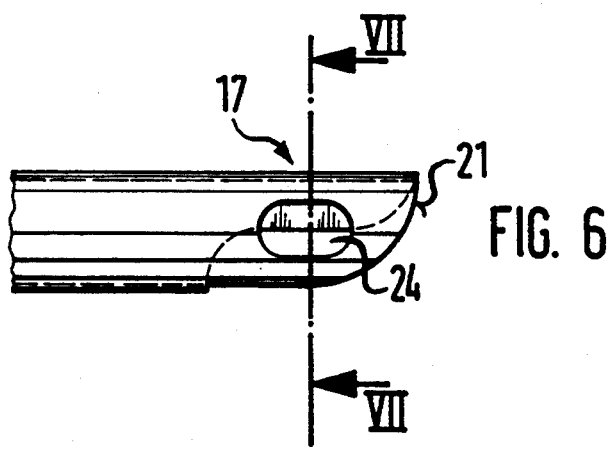
FIG. 6 is a view similar to that of FIG. 4 showing the distal end portion of the shaft rotated by 90° about its longitudinal axis.

As shown in FIG. 3, the shaft 4 is of substantially oval cross-section and has therein a D-cross-section tube 16 for receiving and having fixed therein said viewing lens. The shaft 4 has, as best seen in FIG. 6, a distal end portion 17 formed as a laterally and distally open channel. The remainder of the shaft 4 is of fully tubular cross-section. The tube 16 extends over more than half the cross-section of the shaft 4 as shown in FIG. 3. The tube 16 is located on the side of the shaft 4 on which the shaft 4 ends in the channel-shaped portion 17. The conduit 13 for the fibre 14 continues as a tube 18 in the shaft 4, which tube is of circular cross-section and is disposed on one side of the major semi-axis 19 of the oval cross-section of the shaft 4, as shown in FIG. 3, on the flat side of the D-cross-section tube 16. The tube 18 terminates at its distal end in the region of the channel-shaped portion 17. The tube 18 may, however, terminate a little more proximally of the shaft 4 in order to allow some elastic deformation of the end of the fibre 15 to protect it from breaking.

Figure 2:
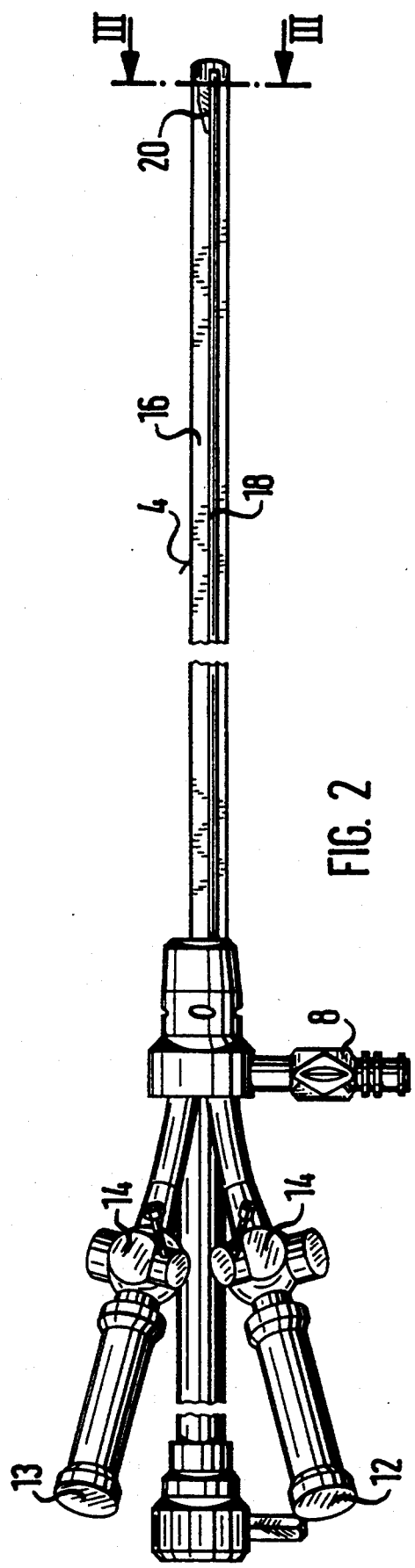
FIG. 2 is a schematic side view of the endoscope with the shaft thereof shown in longitudinal section.

The instrument conduit 12 is defined in the shaft 4 by the flat side of the tube 16, part of the shaft 4 itself and one side of the tube 18. Within the shaft 4, proximate to its distal end, is a wedge-shaped guide 20 which tapers in the proximal direction of the shaft 4 as shown in FIG. 2. The guide 20 ensures that a second instrument introduced into the conduit 12 is deflected away from the fibre 15, as the second instrument emerges from the distal end of the shaft 4, so that the instrument does not damage the fibre 15.

Figure 4:
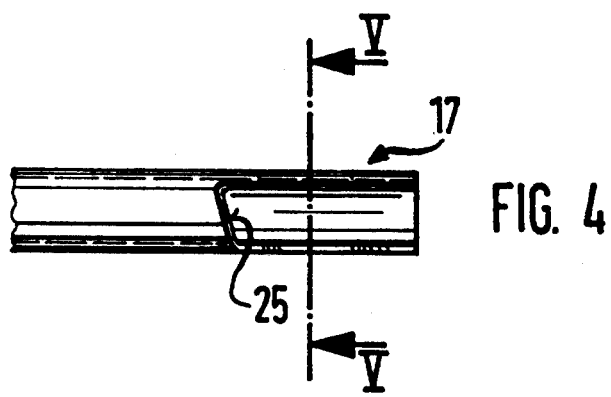
FIG. 4 is an enlarged plan view of the distal end portion of said shaft.
Figure 5:
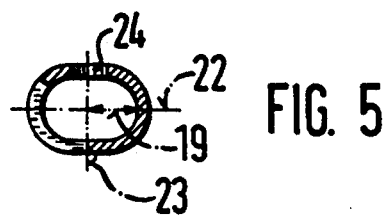
FIG. 5 is a view taken on the lines V—V of FIG. 4.
Figure 7:
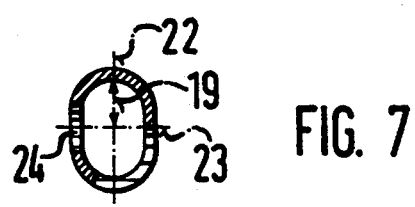
FIG. 7 is a view taken on the lines VII—VII of FIG. 6.

As shown in FIGS. 4 to 7, the channel-shaped end portion 17 of the shaft 4, which extends distally beyond the fully tubular cross-section of the shaft 4, has a sloped back distal end 21, as best seen in FIG. 6 for ease in guiding the shaft 4 between the capsule 5 and the implant 2. As shown in FIGS. 5 and 7, the channel-shaped portion 17 of the shaft 4 is asymetrical, as seen in cross-section with respect to the major cross-sectional axis 22 of the shaft 4. The profile of the portion 17 encloses the semi-axis 19 and extends on one side thereof as far as the minor cross-sectional axis 23 of the shaft 4. A wall of the portion 17 of the shaft 4 on the opposite side of the semi-axis 19, extends beyond the axis 23. The profile of the portion 17 thus extends over a circumferential angle of about 200° of the cross-section of the shaft 4. The angle may be exceeded according to requirements.

The channel-shaped portion 17 also protects the implant 2 from accidental collision with, and damage by, the distal end of the fibre 15 as well as by the distal end of the viewing lens. Such protection alone, however, is insufficient, for example, for the release of the capsule 5, which surrounds the implant 2. An additional viewing window 24 is, therefore, provided in the portion 17. The window 24 is in the form of a recess in the wall of the portion 17, which is approximately oval as seen in FIG. 6. The major axis of the window 24 extends axially of the endoscope. The window 24 is formed in the flat side of the portion 17 which extends beyond the minor axis 23 of the shaft 4. The window 24 could, however, should the occasion arise, be formed in the bottom of the channel provided by the portion 17. The endoscope 1 according to the preferred embodiment, has, however, proved to be particularly advantageous for opening a capsule 5, that is to say, for cutting through the capsule, because the viewing window 24, under the protection of the portion 17 enables the implant 2 to be viewed in relation to the capsule 5 during treatment, the point of treatment being viewed as usual through the viewing lens.

A further sloped end surface 25 is provided in the region of the distal end of the shaft 4, as shown in FIG. 4, at its junction with the channel-shaped portion 17, further to reduce the risk of injury during the axial advance of the shaft 4 into the breast 3.

What is claimed is:

1. An endoscope comprising a tubular shaft for the introduction thereinto of a viewing lens and a treatment instrument, the shaft having a distal end portion which is channel-shaped with a lateral opening forming a viewing window for a viewing lens, and said channel-shaped portion having provided in a wall thereof an additional viewing window for the viewing lens, wherein the shaft is of substantially oval cross-section having major and minor axes, said channel-shaped end portion extending asymmetrically around a portion of the circumference of said oval cross-section, said channel-shaped end portion being defined by a wall which extends up to the minor axis on one side of the major axis of said oval cross-section and which extends beyond said minor axis on the opposite side of said major axis.

2. An endoscope as claimed in claim 1, wherein said channel-shaped end portion has a sloped distal end face.

3. An endoscope as claimed in claim 1, said wall being formed with an aperture therein providing the additional viewing window, the aperture being disposed on one side of the major axis of said oval cross-section.

4. An endoscope as claimed in claim 3, wherein the aperture is disposed in a portion of said wall which extends beyond the minor axis of said oval cross-section.

5. An endoscope as claimed in claim 3, wherein the aperture has an approximately oval contour.

6. An endoscope as claimed in claim 1, wherein the shaft has a front distal end wall at its junction with said channel-shaped portion, said end wall sloping transversely with respect to the longitudinal axis of the shaft.

7. An endoscope as claimed in claim 1, wherein a tube of approximately D-shaped cross-section is disposed within the shaft for receiving a viewing lens.

8. An endoscope as claimed in claim 7, wherein the shaft contains a second tube for guiding a laser transmission optical fibre, the second tube abutting the flat side of the approximately D-shaped cross-section tube.

9. An endoscope as claimed in claim 1, wherein a wedge-shaped optical fibre guide which tapers proximally of the shaft is disposed in the shaft proximate to its distal end and proximally of said channel-shaped end portion.

10. An endoscope as claimed in claim 1, wherein the channel-shaped end portion extends over a circumferential angle of at least about 200° of said oval cross-section.

* * * * *